(12) United States Patent
Sakamoto et al.

(10) Patent No.: US 9,417,231 B2
(45) Date of Patent: Aug. 16, 2016

(54) URINE SAMPLE ANALYZING METHOD AND SAMPLE ANALYZER INCLUDING CLASSIFYING EPITHELIAL CELLS INTO AT LEAST TWO TYPES BASED ON THE CHANGE OF POLARIZATION CONDITION

(71) Applicant: Sysmex Corporation, Kobe-shi, Hyogo (JP)

(72) Inventors: Mitsumasa Sakamoto, Kobe (JP); Masatsugu Ozasa, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 167 days.

(21) Appl. No.: 14/470,496

(22) Filed: Aug. 27, 2014

(65) Prior Publication Data
US 2015/0060647 A1 Mar. 5, 2015

(30) Foreign Application Priority Data
Aug. 30, 2013 (JP) .................................. 2013-178938

(51) Int. Cl.
| | | |
|---|---|---|
| *G01N 21/21* | (2006.01) | |
| *G01N 33/493* | (2006.01) | |
| *G01N 33/50* | (2006.01) | |
| *G01J 1/04* | (2006.01) | |
| *G01J 4/00* | (2006.01) | |
| *G01N 21/53* | (2006.01) | |
| *G01N 21/64* | (2006.01) | |
| *G01N 15/14* | (2006.01) | |

(52) U.S. Cl.
CPC ............. *G01N 33/493* (2013.01); *G01J 1/0429* (2013.01); *G01J 4/00* (2013.01); *G01N 15/1434* (2013.01); *G01N 21/21* (2013.01); *G01N 21/53* (2013.01); *G01N 21/6486* (2013.01); *G01N 33/5005* (2013.01)

(58) Field of Classification Search
CPC .......... G01N 21/21; G01N 2021/0346; G01N 21/6486; G01N 33/493; G01N 30/74
USPC ................. 250/225, 222.2, 573, 576; 435/34, 435/288.7, 31; 356/246, 73, 317, 327, 322
See application file for complete search history.

(56) References Cited

U.S. PATENT DOCUMENTS 5,636,017 A * 6/1997 Bruno ................... G01N 21/05 356/246
6,118,522 A 9/2000 Kanai et al.
(Continued)

FOREIGN PATENT DOCUMENTS

| JP | 2006-17555 A | 1/2006 |
| WO | WO 00/13002 A2 | 3/2000 |

OTHER PUBLICATIONS

Delanghe, J. et al., "The Role of Automated Urine Particle Flow Cytometry in Clinical Practice", *Clinica Chimica Acta*, vol. 301, 2000, pp. 1-18.

*Primary Examiner* — Que T Le
(74) *Attorney, Agent, or Firm* — Brinks Gilson & Lione

(57) ABSTRACT

Disclosed is a urine sample analyzing method comprising: flowing a measurement specimen prepared by mixing a urine sample and reagent through a flow cell; irradiating epithelial cells in the measurement specimen flowing through the flow cell with linearly polarized light and thereby producing scattered light; detecting a change of polarization condition of the scattered light produced by each of the epithelial cells; and classifying the epithelial cells into at least two types based on the change of polarization condition.

20 Claims, 9 Drawing Sheets

(56) References Cited

U.S. PATENT DOCUMENTS 7,674,622 B2  3/2010  Garrett et al.
8,148,101 B2  4/2012  Kim et al.
8,501,482 B2  8/2013  Tanaka et al.
2011/0045525 A1  2/2011  Krockenberger et al.

* cited by examiner

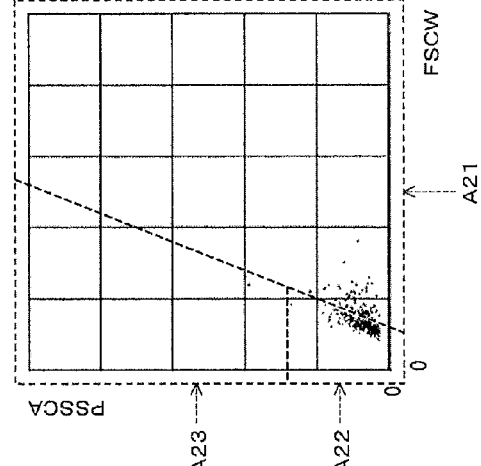
FIG. 8C
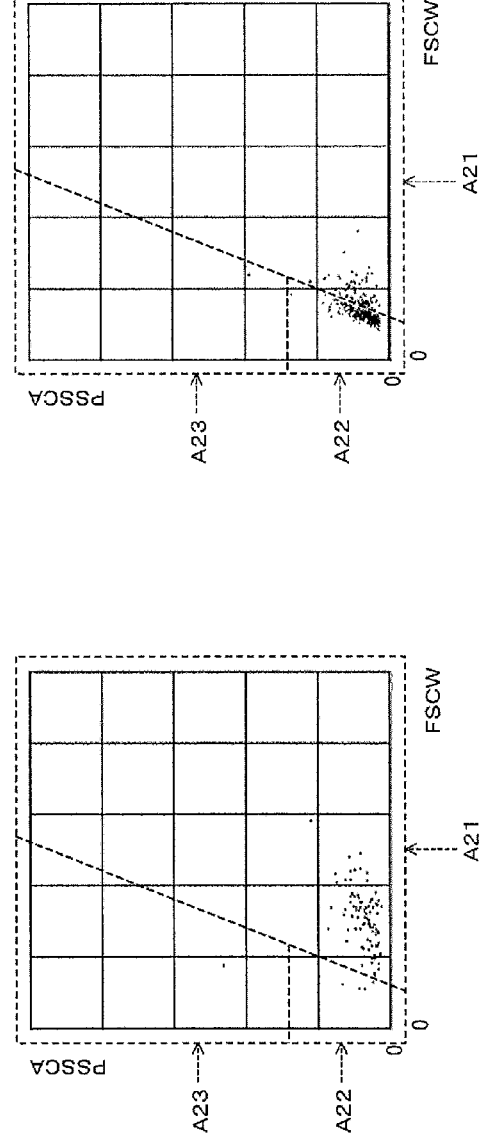
FIG. 8A
FIG. 8D
FIG. 8B

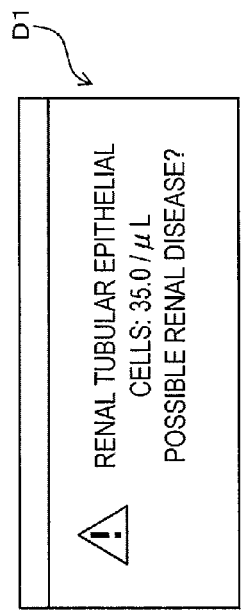
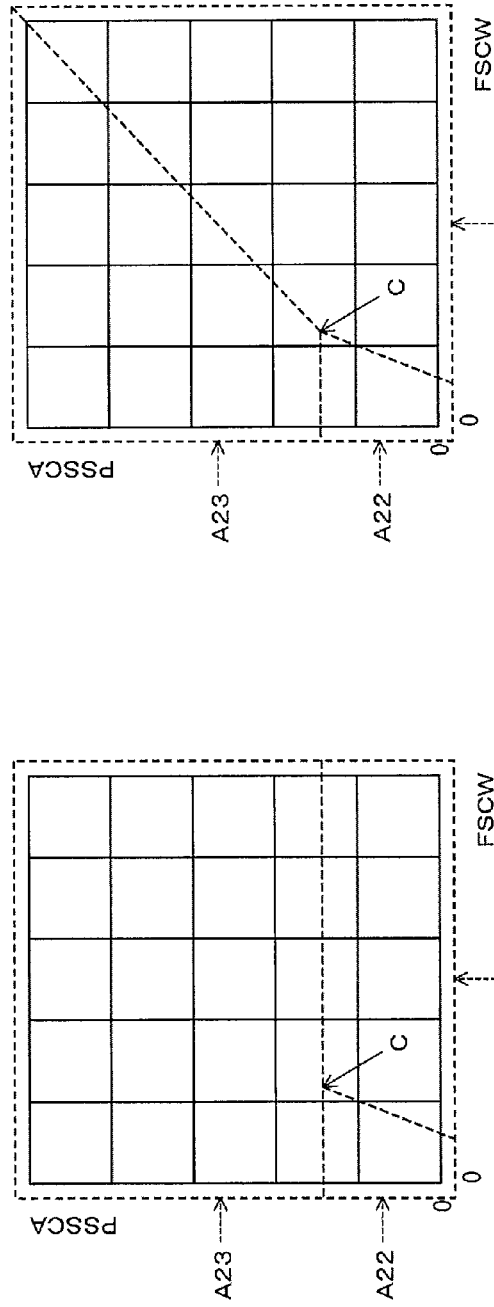

US 9,417,231 B2

URINE SAMPLE ANALYZING METHOD AND SAMPLE ANALYZER INCLUDING CLASSIFYING EPITHELIAL CELLS INTO AT LEAST TWO TYPES BASED ON THE CHANGE OF POLARIZATION CONDITION

RELATED APPLICATIONS

This application claims priority under 35 U.S.C. §119 to Japanese Patent Application No. 2013-178938 filed on Aug. 30, 2013, the entire content of which is hereby incorporated by reference.

FIELD OF THE INVENTION

The present invention relates to a urine sample analyzing method and sample analyzer for analyzing samples.

BACKGROUND OF THE INVENTION

There is known conventional art for detecting particles in urine samples using a flow cytometer. For example, Japanese Laid-open Patent No. 2006-17555 discloses art for classifying the two groups of surface layer squamous type epithelial cells and epithelial cells other than the surface layer squamous type in urine by combining several parameters such as forward scattered light and fluorescent light from particles in a sample using a flow cytometer.

According to that, epithelial cells other than surface layer squamous type epithelial cells, may appear in cases of inflammation and disease, and those are seldom observed in urine samples of healthy individuals. On the other hand, surface layer squamous type epithelial cells are plentiful in urine samples of healthy persons.

Also according to the above document, parameters can be established for estimating the presence/absence of inflammation and disease in a patient who provided a urine sample by calculating the percentage of epithelial cells other than surface layer squamous type epithelial cells relative to the total number of epithelial cells.

Urine samples in cases of suspected disease or inflammation may require detailed information extraction to diagnose the suspected disease or abnormality of the urinary organs. There are several types of epithelial cells of different origin, including squamous epithelial cells, renal tubular epithelial cells, ovoid fat body and the like, which are useful in identifying the origin site of disease and inflammation if the type of epithelial cell contained in the urine sample can be identified.

SUMMARY OF THE INVENTION

The scope of the present invention is defined solely by the appended claims, and is not affected to any degree by the statements within this summary.

A first aspect of the present invention is a urine sample analyzing method comprising: flowing a measurement specimen prepared by mixing a urine sample and reagent through a flow cell; irradiating epithelial cells in the measurement specimen flowing through the flow cell with linearly polarized light and thereby producing scattered light; detecting a change of polarization condition of the scattered light produced by each of the epithelial cells; and classifying the epithelial cells into at least two types based on the change of polarization condition.

A second aspect of the present invention is a urine sample analyzer comprising a preparing section that prepares a measurement specimen by mixing a urine sample and reagent; a flow cell through that flows the measurement specimen prepared by the preparing section; an optical detecting section that irradiates linearly polarized light on particles in the measurement specimen flowing through the flow cell to produce scattered light, and detect a change of polarization condition of the scattered light produced by each of the epithelial cells; and a computer programmed to classify epithelial cells contained in the measurement specimen into at least two types based on the change of the polarization condition A sample analyzing method comprising forming a sample flow of a measurement specimen containing epithelial cells; irradiating the sample flow with a linearly polarized light to trigger a polarization scrambling; and classifying the epithelial cells into at least squamous epithelial cells and other type of epithelial cells based on a degree of the polarization scrambling.

BRIEF DESCRIPTION OF THE DRAWINGS

FIG. 4A illustrates a peak level; FIG. 4B illustrates a width; and FIG. 4C illustrates an area;

FIG. 8A shows comparative results of the visual count results obtained by microscope and results obtained by the embodiment;

FIG. 8B shows the second scattergram obtained by the embodiment;

FIG. 8C shows comparative results of the visual count results obtained by microscope and results obtained by the embodiment;

FIG. 8D shows the second scattergram obtained by the embodiment;

FIG. 9A shows a screen shown on the display;

FIG. 9B shows the region set in the second scattergram in a modification; and

FIG. 9C shows the region set in the second scattergram in a modification.

DETAILED DESCRIPTION OF THE PREFERRED EMBODIMENTS

The present embodiment is a urine sample analyzer for analyzing urine samples which contain particles such as blood cells, bacteria, casts, and epithelial cells. The urine samples to be measured include eliminated urine from a living body, secreted urine, primitive urine, urine of the urinary tract, urine in the bladder, and urine in the urethra.

The embodiment is described below with reference to the drawings.

Figure 1:
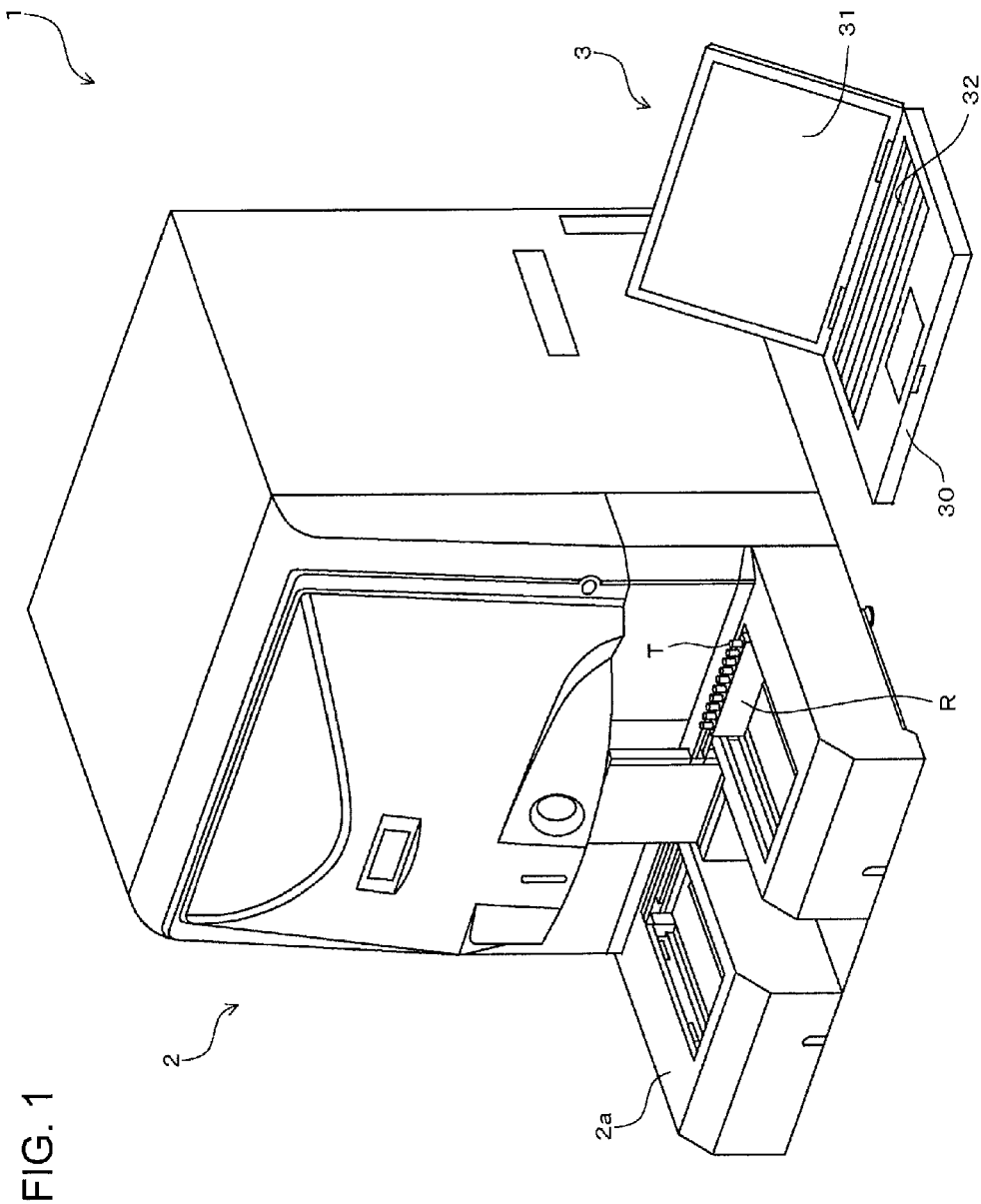
FIG. 1 shows an external view of an embodiment of the urine sample analyzer.

FIG. 1 shows the exterior structure of a urine sample analyzer 1.

The urine sample analyzer 1 has a measuring device 2 for optically measuring particles contained in the urine sample via flow cytometer, and an information processing device 3 for processing the measurement data output from the measuring device 2. A transporting unit 2a is provided in front of the measuring device 2, and the rack R holding a plurality of containers T containing urine samples is moved by the transporting unit 2a. The information processing device 3 is provided with a main body 30, display 31 for displaying analysis results and the like, and an input unit 32 for receiving instructions from the operator.

Figure 2:
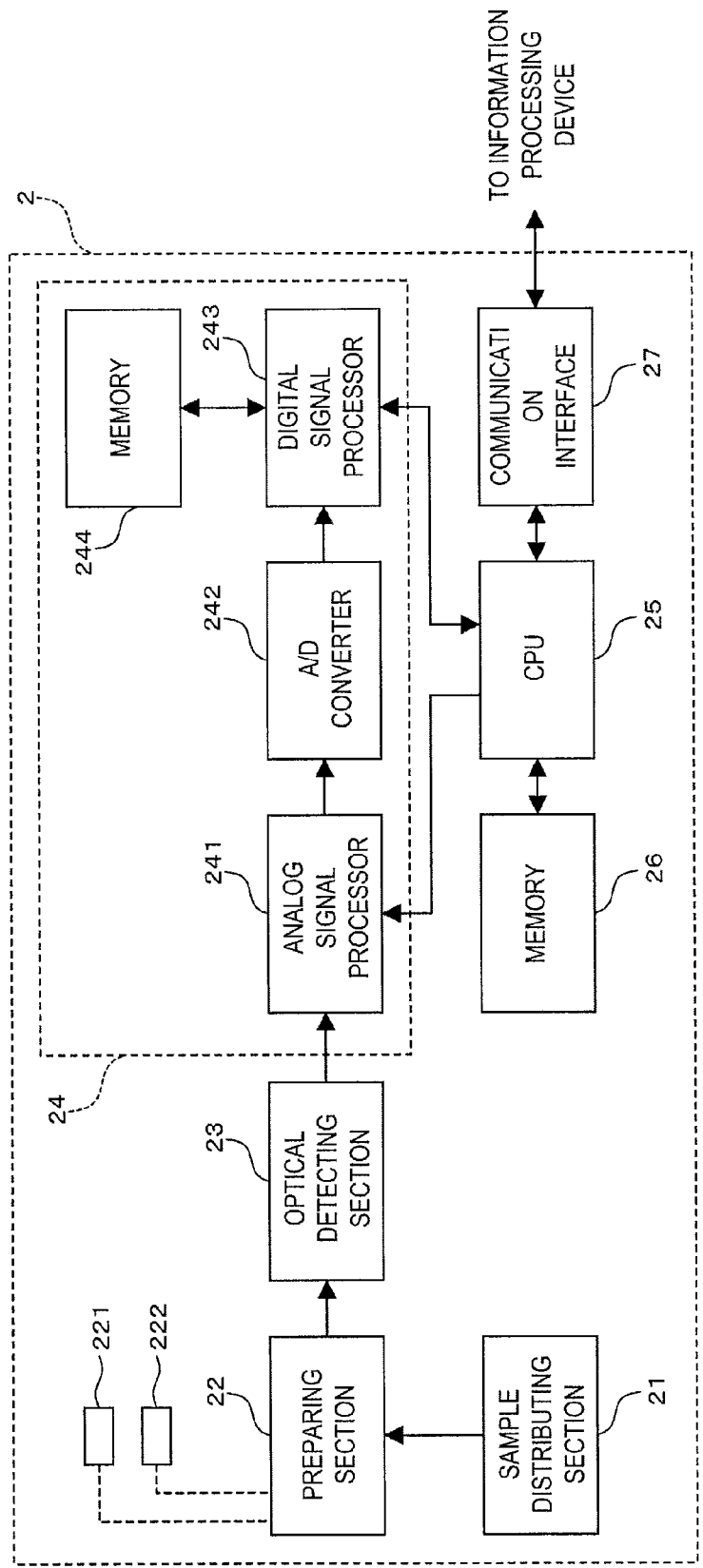
FIG. 2 shows the structure of the measuring device of the embodiment.

FIG. 2 shows the structure of the measuring device 2.

The measuring device 2 includes a sample distributing section 21, a preparing section 22, optical detecting section 23, signal processing section 24, CPU 25, memory 26, and communication interface 27. The signal processing section 24 has an analog signal processor 241, A/D converter 242, digital signal processor 243, and memory 244.

The sample distributing section 21 aspirates a predetermined amount of urine sample from the container T transported by the transporting unit 2a, and supplies the aspirated sample to the preparing section 22. The preparing section 22 has a mixing chamber and a pump (not shown in the drawings). Containers 221 and 222 are connected through a tube to the preparing section 22. The container 221 contains reagent that includes intercalator for specifically staining nucleic acid, and container 222 contains diluting liquid. The sample supplied from the sample distributing section 21 into the mixing chamber is mixed with diluting liquid and reagent from the containers 221 and 222 to prepare the measurement specimen. The measurement specimen prepared in the mixing chamber is supplied together with sheath fluid to a flow cell 205 (refer to FIG. 3) of the optical detecting section 23.

Figure 3:
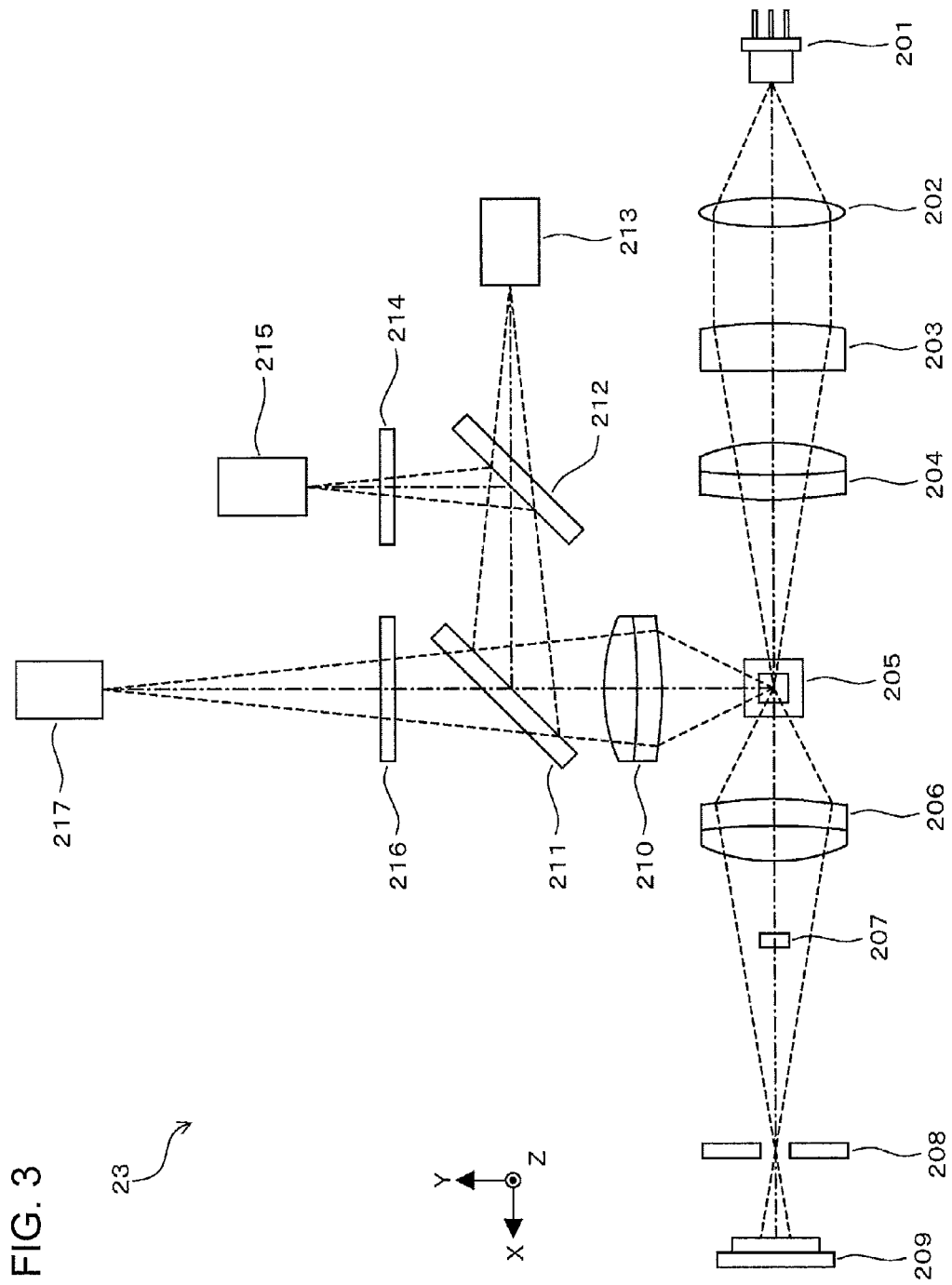
FIG. 3 shows the structure of the optical detecting device of the embodiment.

FIG. 3 is a schematic view showing the structure of the optical detecting section 23.

The optical detection section 23 includes a light source 201, collimator lens 202, cylindrical lens 203, condenser lens 204, flow cell 205, collecting lens 206, beam stopper 207, pinhole 208, FSC detector 209, collecting lens 210, dichroic mirror 211, half mirror 212, SSC detector 213, polarization filter 214, PSSC detector 215, spectral filter 216, and SFL detector 217.

The light source 201 emits laser light having an approximate wavelength of 488 nm in the X-axis positive direction. The laser light emitted from the light source 201 is linearly polarized light. The light source 201 is arranged within the measuring device 2 so that the polarization direction of the linearly polarized light is parallel to the direct (Z-axis direction) of the flow of the measurement specimen running in the flow cell 205. That is, the polarization direction of the light emitted from the light source 201 is perpendicular to the incidence surface when the incidence surface is perpendicular to the Z-axis direction.

The laser light from the light source 201 is converted to parallel rays by the collimator lens 202. The laser light that passes through the collimator lens 202 is converged only in the Y-axis direction by the cylindrical lens 203. The laser light that passes through the cylindrical lens 203 is collected in the Y-axis direction and Z-axis direction by the condenser lens 204. Hence, the laser light emitted from the light source 201 irradiates a beam narrow along the Y-axis direction on the measurement specimen flowing in the Z-axis direction within the flow cell 205. When the laser light irradiates particles in the measurement specimen, forward scattered light is produced in the forward direction (X-axis positive direction) of the flow cell 205, and side scattered light and side fluorescent light are produced in a lateral direction (Y-axis positive direction) of the flow cell 205.

The forward scattered light is collected at the position of the pinhole 208 by the collecting lens 206 arranged on the X-axis positive direction side of the flow cell 205. Among the light emitted from the light source 201, the laser light that passes through the flow cell 205 without illuminating particles in the measurement specimen is collected by the collecting lens 206, and then is blocked by the beam stopper 207 so as to not impinge the detector 209. The forward scattered light that passes through the pinhole 208 is detected by the FSC detector 209. The detector 209 outputs a forward scattered light signal (FSC) based on the detected forward scattered light.

The side scattered light is converged by the collecting lens 210 arranged on the Y-axis positive direction side of the flow cell 205. The side scattered light that passes through the collecting lens 210 is reflected by the dichroic mirror 211. A part of the side scattered light reflected by the dichroic mirror 211 is split by the non-polarizing type half mirror 212. The side scattered light that passes through the half mirror 212 is detected by the SSC detector 213. The SSC detector 213 outputs a side scattered light signal (SSC) based on the detected side scattered light. Another part of the side scattered light reflected by the half mirror 212 impinges the polarization filter 214.

When polarized laser light is irradiated on particles in the measurement specimen, the polarization direction of the side scattered light changes according to the optical rotating power of the component contained in the particle. In the present embodiment, the polarization direction of the laser light irradiating the particles in the measurement specimen is parallel to the flow direction (Z-axis direction) of the measurement specimen flowing through the flow cell 205 (hereinafter, this polarization condition is referred to as the "initial polarization condition"). When the laser light is irradiated to the measurement specimen, the polarization direction of the laser light rotates to a polarization direction that differs from the initial polarization condition. As the polarization of the laser light is partially scrambled by irradiation on particles, the side scattered light produced in the Y-axis positive direction includes rays of various polarization conditions.

Among the rays of the side scattered light produced from the particles, the percentage of rays polarized perpendicular to the initial polarization direction, that is, degree of polarization scrambling, is determined according to the components contained in the particles. As previously described, in the present embodiment several types of epithelial cells are observed contained in the solid components with different inherent polarization characteristics according to type, and the several types of epithelial cells can be classified based on the polarization condition of the side scattered light.

The polarization filter 214 is configured to block the polarized light parallel to the Z-axis direction, and transmit the polarized light parallel to the X-axis direction. The side scattered light that has passed through the polarization filter 214 is referred to as "polarization scrambled side scattered light" or "PSSC light" hereinafter. The polarization scrambled side scattered light is detected by the PSSC detector 215. The PSSC detector 215 outputs a polarization scrambled side scattered light signal (PSSC) based on the detected polarization scrambled side scattered light.

As previously mentioned, the polarization direction of the side scattered light changes from the initial polarization condition according to the optical rotating power possessed by the particle in the measurement specimen. Therefore, the amount of PSSC light that reaches the PSSC detector 215 also differs for each type of particle irradiated by the laser light, and the magnitude of the PSSC signal also differs for each type of particle irradiated by the laser light.

The forward scattered light emitted from the flow cell 205 and the side scattered light passed through the half mirror 212 are directly received by the FSC detector 209 and SSC detector 213, respectively, and do not pass through a polarization filter. Therefore, the FSC detector 209 detects the forward scattered light including rays of nonuniform polarization directions. The SSC detector 213 similarly detects the side scattered light including rays of nonuniform polarization directions. The forward scattered light, similar to the side scattered light, has a polarization direction that changes from the initial polarization direction according to the optical rotating power of the particles in the measurement specimen.

Similar to the side scattered light, the side fluorescent light is converged by the collecting lens 210. The side fluorescent light that has passed through the collecting lens 210 subsequently passes through the dichroic mirror 211 and spectral filter 216, and is then detected by the SFL detector 217. The SFL detector 217 outputs a side fluorescent light signal (SFL) based on the detected side fluorescent light. Fluorescent light may be detected in other angle. For example, the fluorescent light can be detected in forward angle with respect to the irradiating light.

Returning now to FIG. 2, the optical detecting section 23 outputs the forward scattered light signals (FSC), side scattered light signals (SSC), polarization scrambled light signals (PSSC), and side fluorescent light signals (SFL) to the analog signal processor 241. The analog signal processor 241 amplifies, via an amplifier, the electrical signals from each detectors of the optical detecting section 23, and outputs the amplified electrical signals to the A/D converter 242.

The A/D converter 242 converts the electrical signals received from the analog signal processor 241 to digital signals, and outputs the digital signals to the digital signal processor 243. The digital signal processor 243 performs signal processing of the digital signals received from the A/D converter 242. Signal waveforms are obtained which correspond to the forward scattered light side scattered light, polarization scrambled side scattered light, and side fluorescent light produced when the particles pass through the flow cell 205. That is, signal waveforms corresponding to each type of light are obtained for each particle (erythrocytes, leukocytes, epithelial cells, casts, bacteria and the like) contained in the measurement specimen. The obtained signal waveforms are stored in the memory 244.

The CPU 25 calculates a plurality of characteristics parameters (peak level, width, area) corresponding to the forward scattered light, side scattered light, polarization scrambled side scattered light, and side fluorescent light based on the signal waveforms stored in the memory 244.

Figure 4:
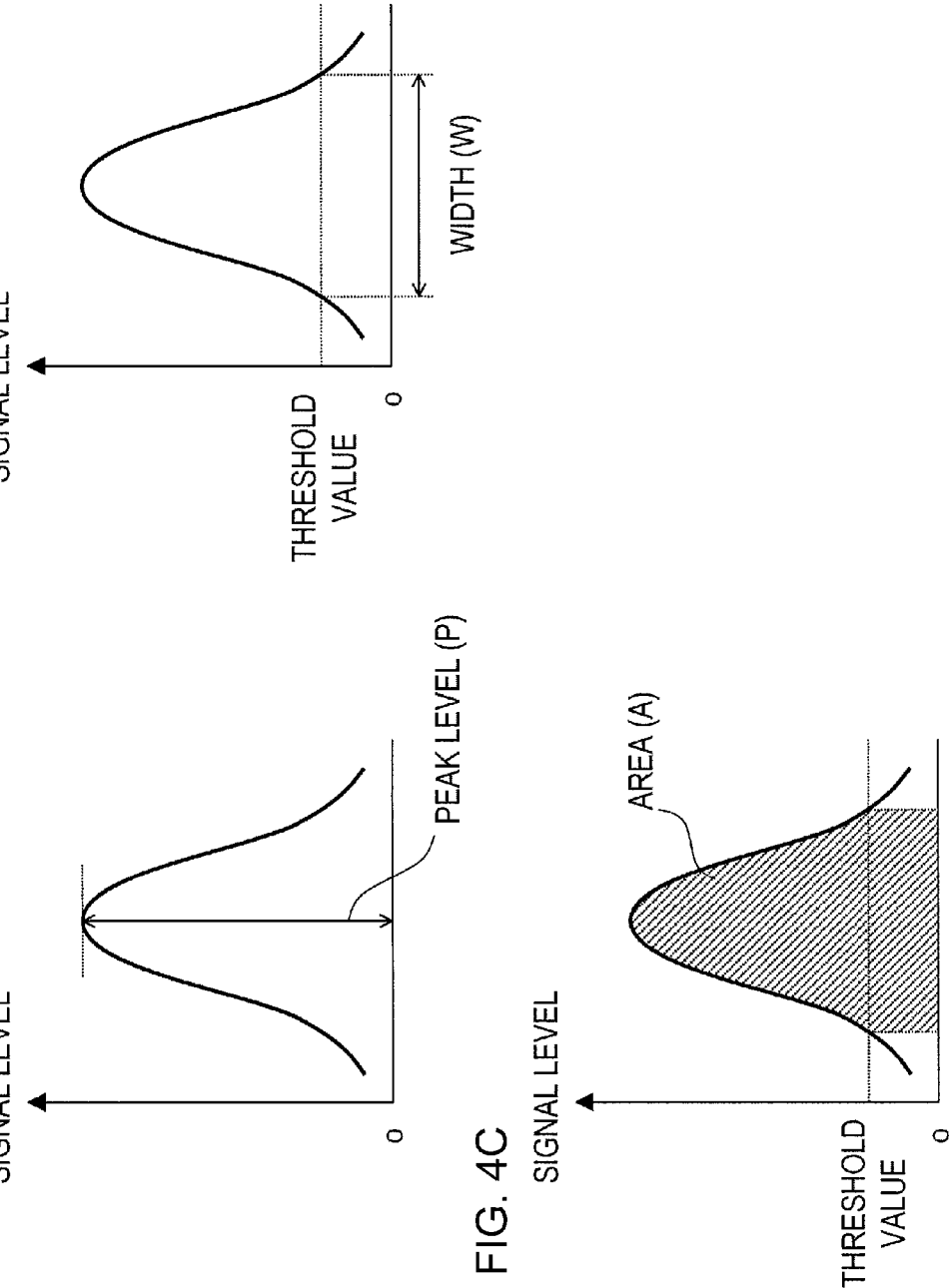
FIGS. 4A through 4C illustrate the characteristic parameters of the embodiment. Specifically.

The peak level (P) is the maximum signal level of the pulse of the signal waveform, as shown in FIG. 4A. The width (W) is the width of the pulse of the signal waveform greater than a predetermined threshold value, as shown in FIG. 4B. The area (A) is the area of the pulse circumscribed by the signal waveform and the line segment extending downward from the origin of the intersection of the signal waveform and predetermined threshold values, as shown in FIG. 4C. The threshold values used in FIGS. 4B and 4C are suitably set according to the characteristics parameters to obtain appropriate characteristics parameters. The calculated characteristics parameters are stored in the memory 26.

The CPU 25 transmits the calculated characteristics parameters of each particle (hereinafter referred to as "measurement data") through the communication interface 27 to the information processing device 3. The CPU 25 receives the control signals from the information processing device 3 through the communication interface 27, and controls each part of the measuring device 2 according to these control signals.

Figure 5:
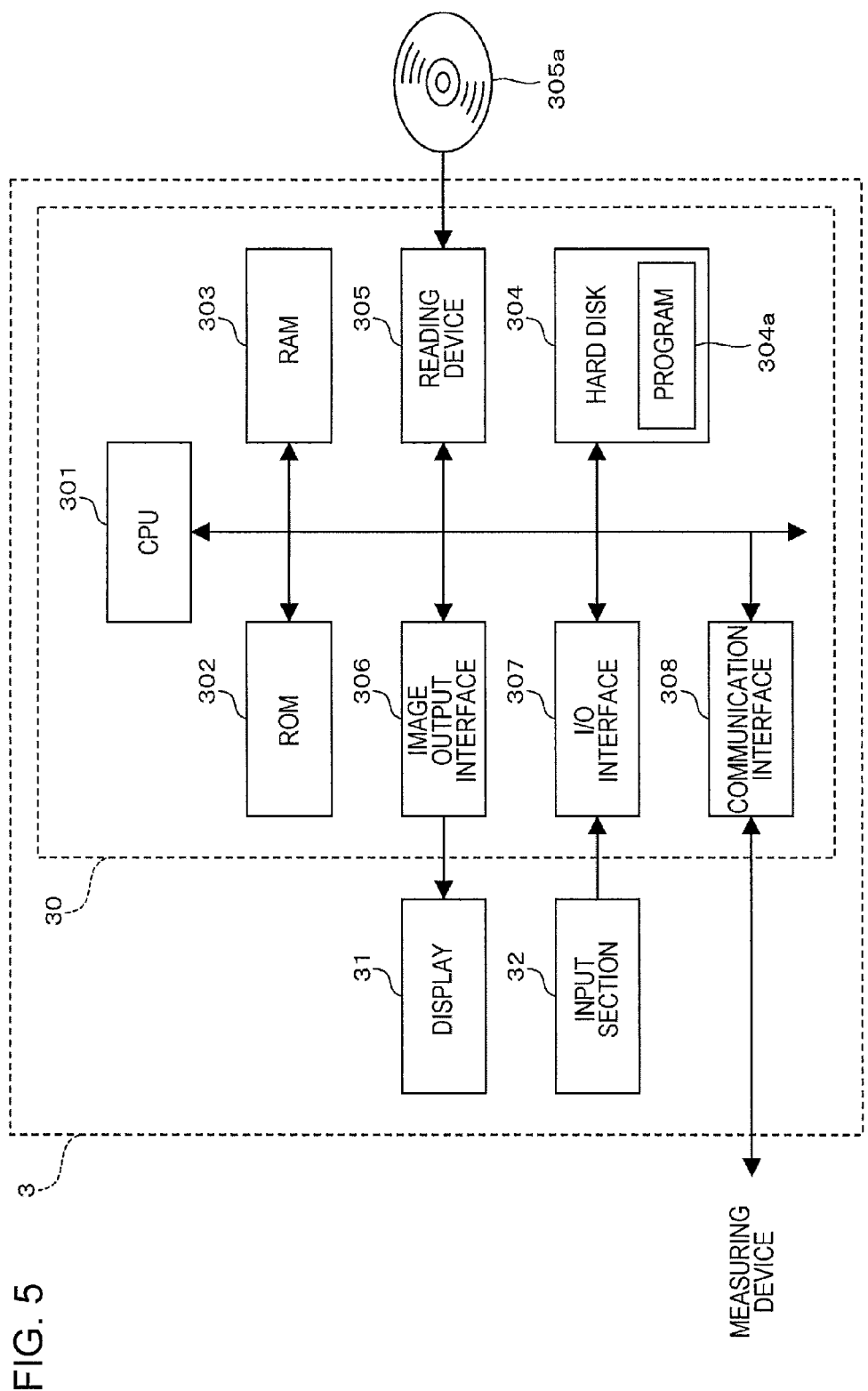
FIG. 5 shows the structure of the information processing device of the embodiment.

FIG. 5 shows the structure of the information processing device 3.

The information processing device 3 is configured by a personal computer that includes a main body 30, display 31, and input section 32. The main body 30 has a CPU 301 ROM 302, RAM 303, hard disk 304, reading device 305, image output interface 306, I/O interface 307, and communication interface 308.

The CPU 301 is capable of executing a computer program stored in the ROM 302 and a computer program loaded in the RAM 303. The RAM 303 is used when reading the computer program stored in the ROM 302 and recorded on the hard disk 304. The RAM 303 is also used as the work area of the CPU 301 when the CPU 301 executes the computer programs.

The hard disk 304 stores an operating system and computer programs, as well as the data used when executing the computer programs that are executed by the CPU 301. The hard disk 304 pre-stores a program 304*a* which performs the process shown in FIG. 6, and sequentially stores measurement data received from the measuring device 2. The reader 305 is a CD drive or DVD drive capable of reading computer programs and data recorded on a recording medium 305*a*. Note that when the program 304*a* is recorded on the recording medium 305*a*, the program 304*a* may be read from the recording medium 305*a* by the reading device 305 and stored on the hard disk 304.

The image output interface 306 outputs image signals corresponding to the image data to the display 31, and the display 31 displays the image based on the image signals. When the operator inputs instructions via the input section 32, the I/O interface 307 receives the input signals. The communication interface 308 is connected to the measuring device 2, and the CPU 301 sends and receives instruction signals and data to/from the measuring device 2 through the communication interface 308.

Figure 6:
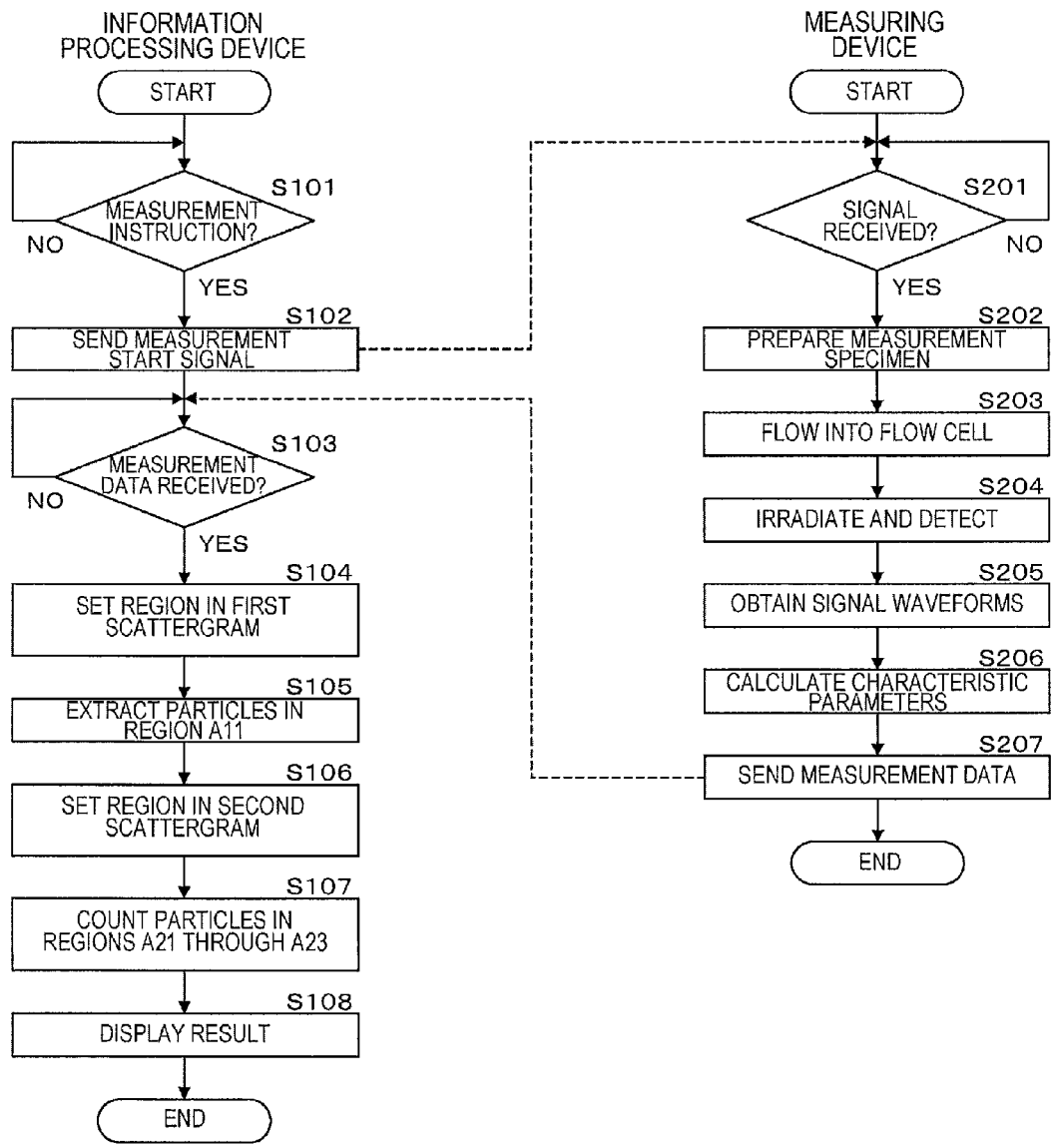
FIG. 6 is a flow chart showing the processes of the measuring device and information processing device of the embodiment.

FIG. 6 is a flow chart showing the processes performed by the measuring device 2 and the information processing device 3.

When the CPU 301 of the information processing device 3 receives a measurement instruction from the operator via the input section 32 (S101: YES), the CPU 301 transmits a measurement start signal to the measuring device 2 (S102). When the CPU 25 of the measuring device 2, on the other hand, receives a measurement start signal from the information processing device 3 (S201: YES), the CPU 25 controls the preparing section 22 to prepare a measurement specimen (S202). The CPU 25 controls the preparing section 22 to supply the prepared measurement specimen to the flow cell 205 so that the measurement specimen flows in the flow cell 205 (S203). Then, laser light emitted from the light source 201 irradiates the measurement specimen flowing through the flow cell 205, and forward scattered light, side scattered light, polarization scrambled side scattered light, and side fluorescent light of each particle contained in the measurement specimen are respectively detected by the FSC detector 209, SSC detector 213, PSSC detector 215, and SFL detector 217 (S204).

The CPU 25 then obtains the signal waveforms corresponding to each type of detected light (S205), and calculates the several characteristics parameters based on the obtained signal waveforms (S206). The CPU 25 then transmits the several calculated characteristics parameters (measurement data) of each particle to the information processing device 3 (S207).

On the other hand, when the CPU 301 of the information processing device 3 receives the measurement data (S103: YES), the CPU 301 sets the regions A11 and A12 in the first scattergram which includes an axis of the width of the forward scattered light signals (FSCW) and an axis of the width of the side fluorescent light signals (FLW) (S104). As shown in FIG. 7A, the CPU 301 plots each particle contained in the measurement data in the first scattergram according to the magnitude of FSCW and the magnitude of FLW.

In FIG. 7A, the region A11 corresponds to the total epithelial cells contained in the measurement specimen, and region A12 corresponds to the casts contained in the measurement specimen. The particles appearing near the origin of the first scattergram, which possesses low FSCW and low FLW, are small particles such as blood cells, bacteria and the like. The CPU 301 extracts the particles, that is, the epithelial cells, in region A11 in the first scattergram (S105).

In the above description particles are plotted in the first scattergram and the particles contained in region A11 of the first scattergram are extracted. However, the regions A11 and A12 of the first scattergram need not necessarily be defined as a diagram or graph. Extraction of particles contained in region A11 also may be accomplished by data processing to extract only those particles related to a specific numerical range via sorting or filtering. Similarly, the regions A21 through A23 of a second scattergram which will be described later need not necessarily be defined as a diagram or graph since the total number of particles contained in regions A21 through A23 may also be obtained by data processing such as sorting or filtering.

The CPU 301 then sets the regions A21 through A23 in the second scattergram which includes an axis of the width of the forward scattered light signal (FSCW) and an axis of the area of the polarization scrambled side scattered light signals (PSSCA) (S106). The CPU 301 plots the particles in region A11 extracted in S105 in the second scattergram according to the magnitude of FSCW and the magnitude of PSSCA, as shown in FIG. 7B.

Figure 7B:
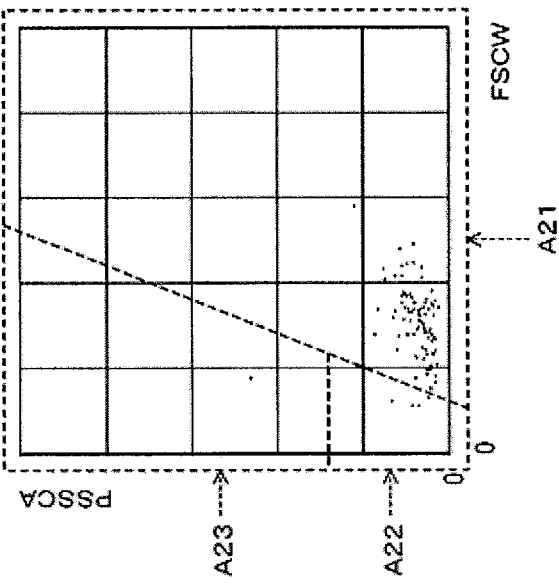
FIG. 7B shows a second scattergram and a region set in the second scattergram of the embodiment.
Figure 7A:
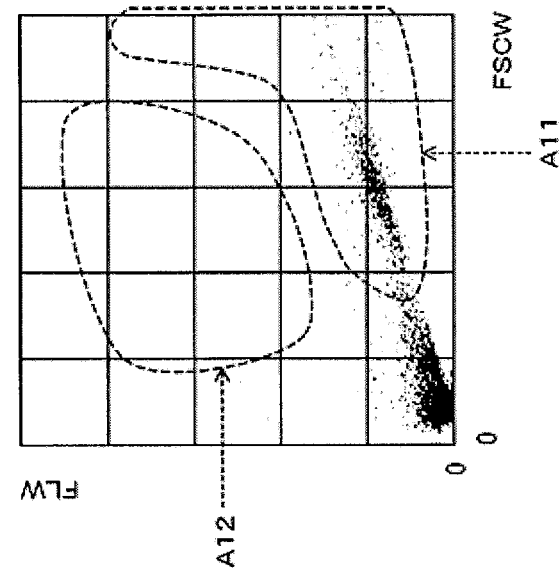
FIG. 7A shows a first scattergram and a region set in the first scattergram.

In FIG. 7B, the region A21 corresponds to the squamous cells, region A22 corresponds to the renal tubular epithelial cells, and region A23 corresponds to the ovoid fat bodies. The CPU 301 counts the particles contained in regions A21 through A23 of the second scattergram, that is, CPU 301 counts the squamous epithelial cells, renal tubular epithelial cells, and ovoid fat bodies.

The vertical axis PSSCA represents an amount of light polarized perpendicularly to the initial polarization direction which is proportional to the degree of polarization scrambling triggered by the particle. The ovoid fat bodies which largely contains the component to scramble polarization, compared to the squamous epithelial cells and renal tubular epithelial cells, are distributed in the region of high PSSCA. The horizontal axis FSCW represents the width of the particle. Therefore, compared to the renal tubular epithelial cells and ovoid fat bodies, the squamous epithelial cells of normally large width are distributed in the region of high FSCW. The renal tubular epithelial cells which contain not so much the component to scramble polarization compared to the ovoid fat bodies, and have small width compared to the squamous epithelial cells, are distributed in the region of low PSSCA and low FSCW. Therefore, the regions A21 through A23 respectively correspond to the squamous epithelial cells, renal tubular epithelial cells, and ovoid fat bodies.

The CPU 301 then shows the particle count obtained in S107 on the display 31 (S108). The processes of the measuring device 2 and the information processing device 3 are thus completed.

The actual count results of a urine sample visually obtained via microscope and the count results of the urine sample obtained by the present embodiment were compared.

FIG. 8A shows the count results of a specific urine sample visually obtained via microscope and the count results of the urine sample obtained by the present embodiment. This urine sample contained 14.0 cells/μL of squamous epithelial cells, 0.0 cells/μL renal tubular epithelial cells, and 0.0 cells/μL ovoid fat bodies by visual results. FIG. 8B shows the second scattergram of the urine sample.

The renal tubule epithelial cells are derived from the epithelium covering the lumen from the proximal tubule, loop of Henle, distal tubule, collecting duct, to the renal papilla. Generally, if there are more than one or two renal tubular epithelial cells contained in a 1 μL urine sample, the patient from whom the urine sample was collected has a high possibility of morbid renal disease, especially at the site where renal tubule epithelial cells present. The ovoid fat bodies are fat granular cells derived from renal tubule epithelial cells. Generally, if there are more than one or two ovoid fat bodies in a 1 μL urine sample, the patient from whom the urine sample was collected has a high possibility of renal disease, for example, nephrotic syndrome.

According to the visual results of FIG. 8A, the renal tubular epithelial cells and ovoid fat bodies contained in 1 μL urine sample is less than one. According to the results of the present embodiment, the renal tubular epithelial cells and ovoid fat bodies contained in 1 μL urine sample is also less than one, similar to the visual results. FIG. 8B shows few particles appeared in regions A22 and A23 respectively corresponding to the renal tubular epithelial cells and ovoid fat bodies.

According to the present embodiment, the operator can determine there is a low possibility of renal disease in the patient based on the few renal tubular epithelial cells in the urine sample collected from the patient, similar to the visual results. Also according to the present embodiment, the operator can determine there is a low possibility the patient has renal disease based on the few ovoid fat bodies in the urine sample collected from the patient, similar to the visual results.

Since squamous epithelial cells are distributed in the mucus membrane near the external urethral orifice and many such cells are found in the urine samples of healthy persons, it is difficult to specify the site of inflammation or disease based on the number of squamous epithelial cells. However, the present embodiment improves the precision of classification of renal tubular epithelial cells and ovoid fat bodies because squamous epithelial cells can be classified from epithelial cells in the urine sample.

FIG. 8C shows the count results obtained visually via microscope and the count results of the present embodiment concerning another urine sample which is different from the urine sample of FIGS. 8A and 8B. This urine sample contained 26.0 cells/μL of squamous epithelial cells, 42.0 cells/μL renal tubular epithelial cells, and 0.0 cells/μL ovoid fat bodies by visual results. FIG. 8D shows the second scattergram of the urine sample.

According to the visual results of FIG. 8C, the number of renal tubular epithelial cells in the 1 μL urine sample was greater than two. The number of ovoid fat bodies contained in the 1 μL urine sample was less than one. According to the results of the present embodiment, the number of renal tubular epithelial cells in the 1 μL urine sample was greater than two, and the number of ovoid fat bodies contained in the 1 μL urine sample was less than one, similar to the visual results. FIG. 8D shows that a large number of particles appeared in the region A22 and few particles appeared in region A23. FIG. 8D suggests that the urine sample contains many renal tubular epithelial cells and few ovoid fat bodies.

According to the present embodiment, the operator can determine there is a high possibility the patient has renal disease at the site where renal tubular epithelial cells presents based on the many renal tubular epithelial cells in the urine sample collected from the patient, similar to the visual results. Also according to the present embodiment, the operator can determine there is a low possibility the patient has renal disease such as nephrotic syndrome based on the few ovoid fat bodies in the urine sample collected from the patient, similar to the visual results.

According to the present embodiment described above, useful information is obtained pertaining to specifying type of epithelial cells contained in the measurement specimen by means of the area of the polarization scrambled side scattered light signal (PSSCA) and the width of the forward scattered light signal (FSCW). This information also may be useful for identifying the site of inflammation or disease.

More specifically, squamous epithelial cells, renal tubular epithelial cells and ovoid fat bodies can be classified by setting regions A21 through A23 in the second scattergram having axes of FSCW and PSSCA. The epithelial cells contained in the urine sample therefore can be finely classified as squamous epithelial cells, renal tubular epithelial cells, and ovoid fat bodies, thus providing information for identifying the site of the disease or inflammation according to the type of epithelial cell.

According to the present embodiment, the number of squamous epithelial cells, renal tubular epithelial cells, and ovoid fat bodies can be obtained and displayed by counting the number of particles in each of the regions A21 through A23 in the second scattergram. Based on the prevalence of renal tubular epithelial cells, the operator therefore can determine there is a high possibility the patient has renal disease at the sites of, for example, the epithelium covering the lumen from the proximal tubule, loop of Henle, distal tubule, collecting duct, to the renal papilla. The operator also can determine the patient has a high possibility of renal disease, such as nephrotic syndrome, based on the prevalence of ovoid fat bodies.

The screen D1 shown in FIG. 9A may be shown on the display 31 of the information processing device 3 in S108 of FIG. 6 when the number of renal tubular epithelial cells or ovoid fat bodies is higher than a threshold number (e.g. two). Screen D1 shows the basis for determining a high possibility of renal disease, that is the number of renal tubular epithelial cells in FIG. 9A, and suggests the possibility of morbidity. In S110 of FIG. 6, the second scattergram shown in FIGS. 8B and 8D also may be displayed.

According to the present embodiment, the polarization direction of the laser light emitted from the light source 201 is parallel to the flow direction (Z-axis direction) of the measurement specimen flowing through the flow cell 205. Therefore, since fluorescent light is produced in the approximate Y-axis direction when the laser light is irradiated in the X-axis positive direction relative to the particles flowing through the flow cell 205, the side scattered light and fluorescent light can be received in approximately the same direction (Y-axis positive direction). The structure of the optical detecting section 23 therefore can be simplified. When the optical detecting section 23 is configured as described above, side fluorescent light is more efficiently detected by the SFL detector 217 arranged on the Y-axis positive side of the flow cell 205.

According to the present embodiment, the PSSC detector 215 can efficiently detect the polarization scrambled side scattered light because the polarization filter 214 blocks the rays of side scattered light that has the same polarization direction as the initial polarization direction.

Although described by way of the above embodiments, the present invention is not limited to these embodiments and may be variously modified.

Although the light source 201 emits linearly polarized light in the above embodiment, the present invention is not limited to this configuration inasmuch as a light source module may be used which combines a generally used light source for emitting non-polarized light and a polarization filter configured to transmit only rays of single polarization direction.

Although the light source 201 is arranged within the measuring device 2 so that the polarization direction of the linearly polarized light is parallel to the direction (Z-axis direction) of the flowing measurement specimen at the laser light irradiation position on the flow cell 205. However, the polarization direction of the laser light emitted from the light source 201 need not necessarily match the flow direction of the measurement specimen, and may be inclined relative to the direction of the flow of the measurement specimen. In this case, the travel direction of the fluorescent light moving from the particle will be distanced from the Y-axis direction compared to the above embodiment. Since the fluorescent light is efficiently detected by the SFL detector 217, the polarization direction of the laser light emitted from the light source 201 preferably matches the flow direction of the measurement specimen as in the above embodiment.

Although the area of the polarization scrambled side scattered light signals (PSSCA) is used as one of the axes in the second scattergram in the above embodiment, other characteristics parameters can be utilized as far as that reflect the degree of polarization scrambling by the particles. For example, the peak level (PSSCP) of the polarization scrambled side scattered light may alternatively be used. In this case, whether the PSSCA or PSSCP is used as the characteristics parameter is appropriately set according to the size of the beam spot of the laser light irradiating the measurement specimen, the speed of the measurement specimen flowing through the flow cell 205, and the amplification of the analog signal processing unit 241.

The characteristics parameter that reflects the degree of polarization scrambling (the vertical axis of the second scattergram) may be obtained from the forward scattered light. As described above, the forward scattered light impinging the FSC detector 209 includes several rays of polarization direction. Therefore, if a half mirror is arranged on the X-axis negative direction side of the FSC detector 209 and the forward scattered light split by the half mirror then passes through a polarization filter, the optical component (polarization scrambled forward scattered light) in a polarization direction different from the initial polarization direction can be received among the forward scattered light from the particles.

Although the two characteristics parameters of the area of the polarization scrambled side scattered light signals (PSSCA) and the width of the forward scattered light signals (FSCW) are combined to classify epithelial cells in the above embodiment, the present invention is not limited to this configuration inasmuch as a single characteristics parameter reflecting the degree of collapse of the initial polarization condition may be used to classify epithelial cells. For example, instead of the second scattergram, a histogram in relation of PSSCA and number of particles can be generated. This histogram may be used as the basis of classification of the epithelial cells. In this case, when most particles are distributed at a high position in the PSSCA, for example, it can be determined that the sample contains ovoid fat bodies. Even when most particles are distributed at a low position in the PSSCA, based on parameters such as mean value, mode value, or area of the histogram, useful information can be provided for determining whether the majority is squamous epithelial cells or renal tubular epithelial cells.

Although the width of the forward scattered light signals (FSCW) is used as the horizontal axis of the second scattergram in the above embodiment, other characteristics parameter reflecting the size of the particles also may be used. For example, the peak level of the forward scattered light signals (FSCP) or the area of the forward scattered light signals (FSCA) may be used. Or by detecting an amount of loss of light by particle which is proportional to project area of the particle may be used. Preferable characteristics parameter of the horizontal axis can be appropriately selected according to the size of the beam spot of the laser light irradiating the measurement specimen, the speed of the measurement specimen flowing through the flow cell 205, and the amplification of the analog signal processing unit 241.

Although the characteristics parameters reflecting the size of the particles are generated based on the forward scattered light signals detected by the optical detecting section 23 in the above embodiment, the present invention is not limited to this configuration inasmuch as the characteristics parameters also may be generated based on the signals detected by an electrical resistance type sensor provided separately in the measuring device 2.

In the above embodiment, a light source 201 is provided in the measuring device 2 so that the polarization direction of the laser light emitted from the light source 201 is uniformed to parallel to the flow direction of the measurement specimen flowing through the flow cell 205. In an alternative, a ½ wavelength plate may be provided on the exit side of the light source 201 so as to adjust the polarization direction of the laser light emitted from the light source 201 to be parallel to the flow direction of the measurement specimen flowing through the flow cell 205.

Although the regions A11, A12, and A21 through A23 are fixed regions determined beforehand in the above embodiment, the regions may be appropriately fine tuned based on the fixed region. The position and shape of the regions A11, A12, and A21 through A23 are not necessarily limited to those shown in FIGS. 7A and 7B, and may be appropriately adjusted to positions and shapes which allow more precise extraction of squamous epithelial cells, renal tubular epithelial cells and ovoid fat bodies.

FIGS. 9A and 9B are modified examples of the regions A21 through A23 set in the second scattergram. When the intersection of the three regions is designated C in the present embodiment, the boundary of the regions A21 and A23 extends from intersection C in a rightward direction in FIG. 9A, and extend from intersection C in an ascending and rightward direction in FIG. 9B. As shown in FIGS. 9A and 9B, ovoid fat bodies distributed in the region of high PSSCA are included in the region S23, squamous epithelial cells distributed in the region of high FSCW are included in region S21, and renal tubular epithelial cells distributed in the region of low PSSCA and low FSCW are included in region A22, similar to the above embodiment.

The structure of the optical system is not necessarily limited to the structure shown in FIG. 3, and may be configured to obtain characteristics parameters to determine the types of epithelial cells based on the degree of optical rotating power. For example, the transmission polarization direction of the polarization filter 214 need not necessarily be parallel to the X-axis direction, and may be inclined from the X-axis direction in a range of the optical rotating power can be observed.

Although urine is used as the sample in the above embodiment, the type of sample is not specifically limited insofar as the sample contained epithelial cells. For example, a sample which contains cervical cells as epithelial cells also may be analyzed. Alternatively, other liquids also may be analyzed. Such liquid may be body fluids other than blood or urine. The body fluids includes cerebrospinal fluid (CSF) filling the subarachnoid space and ventricle, pleural fluid collected in the pleural cavity, ascites fluid collected in the peritoneal cavity, pericardial fluid collected in the pericardial space, joint fluid collected in joints, synovial sac, or tendon sheaths. Peritoneal dialysis (CAPD) dialysis fluid and intraperitoneal cleaning solution are included as a type of body fluid.

Note that the present invention is not limited to the above described embodiment and may be variously modified insofar as such modifications are within the scope of the claims.

What is claimed is:

1. A urine sample analyzing method comprising:
   flowing a measurement specimen prepared by mixing a urine sample and reagent through a flow cell;
   irradiating epithelial cells in the measurement specimen flowing through the flow cell with linearly polarized light and thereby producing scattered light;
   detecting a change of polarization condition of the scattered light produced by each of the epithelial cells; and
   classifying the epithelial cells into at least two types based on the change of polarization condition.

2. The urine sample analyzing method of claim 1, wherein the detection of the change of polarization condition includes to detect at least a part of the scattered light produced by a polarization scrambling which the epithelial cell triggered.

3. The urine sample analyzing method of claim 1, wherein the detection of the change of polarization condition includes to detect a part of the scattered light having a polarization condition that differs from that of the irradiating light.

4. The urine sample analyzing method of claim 1, wherein the irradiating light is polarized parallel to the flow direction of the measurement specimen; and
   the detection of the change of polarization condition includes to detect a part of the scattered light having a polarization direction perpendicular to that of the irradiating light.

5. The urine sample analyzing method of claim 1, further comprising
   transmitting a part of the scattered light which having a polarization direction different from that of the irradiating light to a detector via a polarization filter; and
   blocking at least a part of the scattered light having a polarization direction same with that of the irradiating light via the polarization filter.

6. The urine sample analyzing method of claim 1, further comprising
   obtaining sizes of the epithelial cells based on other part of the light produced by the irradiation; and
   wherein the epithelial cells are classified based on the changes of the polarization conditions and the sizes.

7. The urine sample analyzing method of claim 1, wherein epithelial cells are classified at least as squamous epithelial cells and renal tubular epithelial cells.

8. The urine sample analyzing method of claim 1, wherein epithelial cells are classified as squamous epithelial cells, renal tubular epithelial cells, and ovoid fat bodies.

9. The urine sample analyzing method of claim 8, further comprising
counting the respective classified squamous epithelial cells and renal tubular epithelial cells.

10. The urine sample analyzing method of claim 9, further comprising
displaying a message suggesting a possibility of disease when the number of the renal tubular epithelial cells is higher than a threshold.

11. The urine sample analyzing method of claim 1, further comprising
obtaining sizes of the epithelial cells based on other part of the light produced by the irradiation; and
plotting the epithelial cells on a coordinate space having an axis of a degree of the change of the polarization condition and an axis of size.

12. A urine sample analyzer comprising
a preparing section that prepares a measurement specimen by mixing a urine sample and reagent;
a flow cell through that flows the measurement specimen containing epithelial cells prepared by the preparing section;
an optical detecting section that irradiates linearly polarized light on particles in the measurement specimen flowing through the flow cell to produce scattered light, and detects a change of polarization condition of the scattered light produced by each of the epithelial cells; and
a computer programmed to classify epithelial cells contained in the measurement specimen into at least two types based on the change of the polarization condition.

13. The urine sample analyzer of claim 12, wherein
the optical detecting section detects at least a part of the scattered light produced by a polarization scrambling which the particle triggered.

14. The urine sample analyzer of claim 12, wherein
the optical detecting section detects a part of the scattered light having a polarization condition that differs from that of the irradiating light.

15. The urine sample analyzer of claim 12, wherein
the optical detecting section irradiates light polarized parallel to the flow direction of the measurement specimen, and detects scattered light polarized perpendicular to the polarization direction of the irradiating light.

16. The urine sample analyzer of claim 12, wherein
the optical detecting section comprises:
a detector arranged to detect a part of the scattered light produced by particles; and
a polarization filter arranged in the light path between the detector and the flow cell to transmit a part of the scattered light having a polarization direction different from that of the irradiating light to the detector and to block at least a part of the scattered light having a polarization direction same with that of the irradiating light.

17. The urine sample analyzer of claim 12, wherein
the optical detecting section comprises:
a first detector that converts at least a part of the scattered light which has a polarization condition different from that of the irradiating light to a first signal; and
a second detector that converts at least another part of the scattered light to a second signal indicative of size of particle,
wherein the computer is programmed to classify the epithelial cells based on the first signal and the second signal.

18. The urine sample analyzer of claim 12, wherein
the computer is programmed to classify the epithelial cells into at least squamous epithelial cells and renal tubular epithelial cells.

19. A sample analyzing method comprising
forming a sample flow of a measurement specimen containing epithelial cells;
irradiating the sample flow with a linearly polarized light to trigger a polarization scrambling; and
classifying the epithelial cells into at least squamous epithelial cells and other type of epithelial cells based on a degree of the polarization scrambling.

20. The sample analyzing method of claim 19 further comprising
preparing the measurement specimen by mixing a sample and reagent, wherein the sample is selected from urine and body fluid which is other than blood or urine.

* * * * *